(12) United States Patent
Chadwick et al.

(10) Patent No.: US 12,337,056 B2
(45) Date of Patent: Jun. 24, 2025

(54) TOPICAL COMPOSITIONS AND METHODS

(71) Applicant: MARY KAY INC., Addison, TX (US)

(72) Inventors: Edward Chadwick, Addison, TX (US);
Michael Frushour, Addison, TX (US);
Tiffany Carle, Addison, TX (US)

(73) Assignee: MARY KAY INC., Addison, TX (US)

( * ) Notice: Subject to any disclaimer, the term of this patent is extended or adjusted under 35 U.S.C. 154(b) by 546 days.

(21) Appl. No.: 16/425,646

(22) Filed: May 29, 2019

(65) Prior Publication Data
US 2019/0365629 A1 Dec. 5, 2019

Related U.S. Application Data

(60) Provisional application No. 62/677,273, filed on May 29, 2018.

(51) Int. Cl.
| A61K 8/73 | (2006.01) |
| A61K 8/20 | (2006.01) |
| A61K 8/34 | (2006.01) |
| A61K 8/35 | (2006.01) |
| A61K 8/362 | (2006.01) |
| A61K 8/41 | (2006.01) |
| A61Q 19/00 | (2006.01) |

(52) U.S. Cl.
CPC .............. *A61K 8/73* (2013.01); *A61K 8/20* (2013.01); *A61K 8/345* (2013.01); *A61K 8/35* (2013.01); *A61K 8/362* (2013.01); *A61K 8/41* (2013.01); *A61K 8/735* (2013.01); *A61Q 19/00* (2013.01)

(58) Field of Classification Search
None
See application file for complete search history.

(56) References Cited

U.S. PATENT DOCUMENTS

| 2,798,053 A | 7/1957 | Brown |
| 3,755,560 A | 8/1973 | Dickert et al. |
| 4,421,769 A | 12/1983 | Dixon et al. |
| 4,509,949 A | 4/1985 | Huang et al. |
| (Continued) |

FOREIGN PATENT DOCUMENTS

| CN | 101495090 | 7/2009 |
| CN | 101686903 | 3/2010 |
| (Continued) |

OTHER PUBLICATIONS

Ma'or et al. (Dead-Sea mineral-based cosmetics-Facts and illusions)Isr J MedSci 1996; 32 (Suppl 3) 28-35. (Year: 1996).*

(Continued)

*Primary Examiner* — Isis A Ghali
(74) *Attorney, Agent, or Firm* — NORTON ROSE FULBRIGHT US LLP

(57) ABSTRACT

The present invention relates generally to methods of use and compositions useful for reducing the appearance of fine lines and wrinkles, moisturizing skin, promoting hydration, strengthening and repairing skin, reducing inflammation and redness, reducing oxidizing agents, protecting against pollution, reducing skin desquamation, reducing skin roughness, increasing skin lubricity, improving skin barrier function, and firming and conditioning skin. The composition includes a combination of one or more of saccharide isomerate, sodium carrageenan, sea salt, and sodium hyaluronate.

13 Claims, 4 Drawing Sheets

(56) References Cited

U.S. PATENT DOCUMENTS

| | | | |
|---|---|---|---|
| 4,599,379 | A | 7/1986 | Flesher et al. |
| 4,628,078 | A | 12/1986 | Glover et al. |
| 4,835,206 | A | 5/1989 | Farrar et al. |
| 4,849,484 | A | 7/1989 | Heard |
| 5,011,681 | A | 4/1991 | Ciotti et al. |
| 5,100,660 | A | 3/1992 | Hawe et al. |
| 5,087,455 | A | 11/1992 | Niwa et al. |
| 5,766,575 | A | 6/1998 | Crotty et al. |
| 5,925,348 | A * | 7/1999 | Riley .................. A61K 8/66 424/94.5 |
| 2005/0196370 | A1 | 9/2005 | Yu et al. |
| 2008/0233075 | A1* | 9/2008 | Sokolinsky ............ A61K 8/985 424/78.03 |
| 2008/0305057 | A1* | 12/2008 | Fox .................... A61Q 17/04 424/60 |
| 2010/0247694 | A1* | 9/2010 | Di Bartolomeo .... A61K 9/0043 424/769 |
| 2016/0361346 | A1* | 12/2016 | Ripley ................ A61K 8/676 |
| 2017/0027856 | A1 | 2/2017 | Florence et al. |
| 2017/0216165 | A1 | 8/2017 | Traynor et al. |
| 2017/0252293 | A1* | 9/2017 | Brumbaugh ......... A61Q 19/007 |
| 2018/0104174 | A1 | 4/2018 | Courtin et al. |

FOREIGN PATENT DOCUMENTS

| | | |
|---|---|---|
| CN | 103027884 | 4/2013 |
| CN | 103720623 | 4/2014 |
| CN | 104095790 | 10/2014 |
| CN | 104306195 | 1/2015 |
| CN | 104473788 | 4/2015 |
| CN | 104887590 | 9/2015 |
| CN | 104887612 | 9/2015 |
| CN | 104906021 | 9/2015 |
| CN | 105030552 | 11/2015 |
| CN | 105039032 | 11/2015 |
| CN | 105055297 | 11/2015 |
| CN | 105168095 | 12/2015 |
| CN | 105456174 | 4/2016 |
| CN | 105476944 | 4/2016 |
| CN | 105560156 | 5/2016 |
| CN | 105616281 | 6/2016 |
| CN | 105616325 | 6/2016 |
| CN | 105640867 | 6/2016 |
| CN | 105687080 | 6/2016 |
| CN | 105832619 | 8/2016 |
| CN | 105943475 | 9/2016 |
| CN | 106420454 | 2/2017 |
| CN | 106726790 A * | 5/2017 |
| CN | 108024947 | 5/2018 |
| CN | 108025021 | 5/2018 |
| KR | 20040024004 | 3/2004 |
| KR | 20050098119 | 10/2005 |
| KR | 10-0554860 | 2/2006 |
| KR | 10-0593707 | 6/2006 |
| KR | 20070091758 | 9/2007 |
| KR | 10-0814651 | 3/2008 |
| KR | 20080034890 | 4/2008 |
| KR | 10-0828494 | 5/2008 |
| KR | 20080054627 | 6/2008 |
| KR | 20080068027 | 7/2008 |
| KR | 20090017220 | 2/2009 |
| KR | 10-0918518 | 9/2009 |
| KR | 20100030453 | 3/2010 |
| KR | 20100133711 | 12/2010 |
| KR | 20100136537 | 12/2010 |
| KR | 20120016524 | 2/2012 |
| KR | 10-1121949 | 3/2012 |
| KR | 20120069198 | 6/2012 |
| KR | 20130014143 | 2/2013 |
| KR | 20140040338 | 4/2014 |
| KR | 101464043 B1 * | 11/2014 |
| KR | 20150027975 | 3/2015 |
| KR | 20150096999 | 8/2015 |
| KR | 10-1578408 | 12/2015 |
| KR | 20160139993 | 12/2016 |
| KR | 10-1699802 | 1/2017 |
| KR | 10-1752312 | 6/2017 |
| KR | 20170092281 | 8/2017 |
| KR | 20170099656 | 9/2017 |
| WO | WO 2008/046606 | 4/2008 |
| WO | WO 2008154483 | 12/2008 |
| WO | WO 2010043346 | 4/2010 |
| WO | WO-2018085535 A2 * | 5/2018 ............. A61K 36/53 |

OTHER PUBLICATIONS

Quist et al. "Anti-inflammatory effect of topical formulations containing sea silt and sea salt on human skin in vivo during cutaneous microdialysis", Journal Compilation; Acta Dermo-Venerologica, pp. 1-3 (Year: 2011).*

Varothai et al. "Moisturizers for patients with atopic dermatitis", Asian Pac J Allergy Immuno., 31: 91-98 (Year: 2013).*

Harari "Beauty is not only skin deep: the Dead Sea features and cosmetics", Anales de Hidrologia Medica, vol. 5, No. 1, 75-88 (Year: 2012).*

Rusch et al. (Comparative thermographic assessment of lower leg baths in medicinal mineral waters), Recent Advance in Medical Thermology, pp. 335-540 (Year: 1984).*

AesthiGel*, Barnet Products Corporation, 2015, 2 Pages.

Sodium Hyaluronate Powder Product Data Sheet, Tri-K Industries, Inc., 2008, 1 page.

International Search Report and Written Opinion Issued in International Application No. PCT/US2019/034373, dated Sep. 11, 2019.

"Corneotherapy." Jan. 24, 2016 and California SCC, Barnet.

"EPIDERMIST 4.0: New Skin Builder." Cosmetics Business, Jul. 22, 2013,https://www.cosmeticsbusiness.com/news/article_page/EPIDERMIST_40_New_Skin_Builder/89190. Accessed Oct. 8, 2021.

Benoiderm Efficacy Report. Technical Dossier 12-073GB Oct. 2012, 46 pages.

Office Action issued in Corresponding Chinese Application No. 201910456782.2, dated Oct. 14, 2022 (English Translation provided).

Search Report issued in Corresponding Chinese Application No. 201910456782.2, dated Oct. 10, 2022 (English Translation provided).

"Mild Kit" *acne intelligence*, https://acneintelligence.com/products/mild-kit. Accessed May 2, 2023.

"Pulp Cosmetics India Banished—Retinal + Niacinamide Serum" *INCI Decoder*, https://incidecoder.com/products/pulp-cosmetics-india-banished-retinal-niacinamide-serum. Accessed May 2, 2023.

"Skinbetter—Hydration Boosting Cream 50 ml" *aestheti.care Medspa*, https://greatskinkc.com/product/skinbetter-hydration-boosting-cream-50-ml/. Accessed May 2, 2023.

"Skinbetter Hydration Boosting Cream" *Skin Beautiful RX*, https://skinbeautifulrx.com/products/skinbetter-hydration-boosting-cream. Accessed May 2, 2023.

"The Acne Intelligence Skin Trifecta" *acne intelligence*, https://acneintelligence.com/products/skin-trifecta. Accessed May 2, 2023.

* cited by examiner

TOPICAL COMPOSITIONS AND METHODS

CROSS-REFERENCE TO RELATED APPLICATIONS

The present application claims priority to U.S. provisional patent application 62/677,273 filed May 29, 2018, the disclosure of which is hereby incorporated by reference in its entirety.

BACKGROUND OF THE INVENTION

A. Field of the Invention

The present invention relates generally to compositions that can be used in topical compositions, such as cosmetic compositions used to reduce the appearance of fine lines and wrinkles around the eyes.

B. Description of Related Art

Ageing, chronic exposure to adverse environmental factors, malnutrition, fatigue, etc., can change the visual appearance, physical properties, or physiological functions of skin and tissue in ways that are considered visually undesirable. The most notable and obvious changes include the development of fine lines and wrinkles, loss of elasticity, increased sagging, loss of firmness, loss of color evenness or tone, coarse surface texture, and mottled pigmentation. Less obvious but measurable changes which occur as skin and tissue ages or endures chronic environmental insult include a general reduction in cellular and tissue vitality, reduction in cell replication rates, reduced cutaneous blood flow, reduced moisture content, accumulated errors in structure and function, alterations in the normal regulation of common biochemical pathways, and a reduction in the skin's and tissue's ability to remodel and repair itself. Many of the alterations in appearance and function of the skin are caused by changes in the outer epidermal layer of the skin, while others are caused by changes in the lower dermis. Regardless of the stimulus for skin damage, when damage occurs, numerous natural and complex biochemical mechanisms are set into motion in attempts to repair the damage.

Extrinsic and intrinsic factors that can damage the skin or tissues are difficult or impossible to avoid. When exposed to some extrinsic factors, when damaged, or through intrinsic factors, the production of structural proteins and proteins involved in elasticity and binding of the skin and tissue can decrease (e.g., elastin, collagen, laminin, and fibronectin). The decrease in such proteins can lead to undesired outcomes such as sagging, decreased firmness, etc. of the skin. Thus, compositions and methods are desired that can firm and condition the skin and/or increase production of elastin, collagen, laminin, and/or fibronectin.

Maintaining moisture of the skin and/or hair helps overcome some unwanted changes in skin. However, maintaining moisture of the skin can be difficult. This is especially true for subjects with skin that is more dry than average (dry skin type). Exposure to chemicals, solvents, washing, cosmetics, fabrics, or dry environments are some of the many ways that skin can lose moisture.

Skin and hair can lose moisture as a result of cleansing and/or freshening the skin and hair. Skin and hair cleansing and/or freshening compositions are typically applied to skin and/or hair and rinsed-off with water (e.g., rinse-off product), robbing the skin of natural oils and lipids. Further, cleansing and freshening compositions oftentimes have ingredients that can be caustic to the surfaces to be cleansed. For instance, many types of cleansers and fresheners use certain surfactants that can cause skin irritation.

Cosmetics, including makeup foundations and masks, can cause drying of the skin. Foundations are typically applied to skin and left on the skin so that additional makeup may be applied or to hide the appearance of unwanted blemishes or colors. Some problems associated with foundations include skin irritation, stability, lack of adequate effectiveness, difficulty in applying to skin, and drying of the skin. Masks are typically applied to skin and left on the skin for a period of time to allow the claimed benefits of the mask to occur. Problems associated with masks include skin irritation, stability, lack of adequate effectiveness, difficulty in applying to skin, and drying of the skin. Many masks also exfoliate the skin, which can cause or exacerbate irritation, sensitivity, and dryness.

Moisturizers are complex mixtures of chemical agents specially designed to make the external layers of the skin (epidermis) softer and more pliable. They increase the skin's hydration (water content) by reducing evaporation. Naturally occurring skin lipids and sterols, as well as artificial or natural oils, humectants, emollients, lubricants, etc., may be part of the composition of commercial skin moisturizers. They usually are available as commercial products for cosmetic and therapeutic uses, but can also be made at home using common pharmacy ingredients. However, moisturizers are not perfect. Some problems associated with moisturizers include unpleasant tactile properties (e.g., heavy, greasy, or sticky feel), instability, skin-irritation, or insufficient moisturization capabilities.

Others have attempted to create compositions and methods that reduce the appearance of fine lines and wrinkles around the eyes, moisturize skin, promote hydration, strengthen and repair skin, and firm and condition skin. However, many attempts have been ineffective, only addressed one or a few of the undesired outcomes, or caused unacceptable side effects themselves, such as skin irritation or an allergic response. Further, not every effective composition will be compatible with every skin or tissue type. Thus, there is a need for new products that are effective at reducing the appearance of fine lines and wrinkles around the eyes, moisturizing skin, promoting hydration, strengthening and repairing skin, and firming and conditioning skin.

SUMMARY OF THE INVENTION

The inventors have identified a solution to the problems associated with current cosmetic products. The solution resides in a combination of ingredients including saccharide isomerate, sodium carrageenan, sodium hyaluronate, and sea salt. The combination can be used to create topical compositions that reduce the appearance of fine lines and wrinkles, moisturize skin, promote hydration, strengthen and repair skin, reduce inflammation and redness, reduce oxidizing agents, protects against pollution, reduce skin desquamation, reduce skin roughness, increase skin lubricity, and/or firm and condition skin. Saccharide isomerate was shown to increase keratinocyte production of filaggrin and occludin, decrease TNF-α production, increase skin conductance, and increase antioxidant capacity. Sodium carrageenan was shown to increase epidermal production of hyaluronic acid, dermal production of hyaluronic acid, stratum corneum production of ceramides, and epidermal production of ceramides.

In some aspects, there is disclosed a topical composition that includes any one of, any combination of, or all of saccharide isomerate, sodium carrageenan, sodium hyaluronate, and sea salt. The amounts of the ingredients within the composition can vary (e.g., amounts can be as low as 0.000001% to as high as 98% w/w or any range therein). In some aspects, the topical composition includes 0.001 to 5% w/w of saccharide isomerate, 0.001 to 5% w/w of sodium carrageenan, 0.0001 to 5% w/w of sea salt, and 0.0001 to 1% w/w of sodium hyaluronate. In some instances, the composition includes an effective amount of saccharide isomerate, sodium carrageenan, and sea salt. In some instances, the composition includes an amount of saccharide isomerate, sodium carrageenan, and sea salt effective to do one or more of the following: reduce the appearance of fine lines and wrinkles, moisturize skin, promote hydration, strengthen and repair skin, reduce inflammation and redness, reduce oxidizing agents, protect against pollution, reduce skin desquamation, reduce skin roughness, increase skin lubricity, and/or firm and condition skin. In some instances, the composition includes an effective amount of sodium hyaluronate to increase skin moisturization, improve skin barrier function, reduce skin desquamation, reduce skin roughness, increase skin lubricity, and/or firm and condition skin. In some instances, the composition includes an effective amount of saccharide isomerate to condition and moisturize the skin, decrease TNF-α production, increase skin conductance, and/or increase antioxidant capacity, and/or an effective amount of sodium carrageenan and sea salt to promote hydration of the skin and strengthen and repair skin, increase epidermal and dermal production of hyaluronic acid, and/or increase stratum corneum and epidermal production of ceramides.

In some instances, the composition further includes water. In some instances, the composition includes 75 to 95% w/w of water. In some instances, the composition further contains one or more of glycerin, disodium EDTA, benzophenone-4, butylene glycol, triethanolamine, bis-PEG-18 methyl ether dimethyl silane, xanthan gum, c-isostearyl alcohol, and/or diisostearyl malate. In some instances, the composition contains one or more of 0.5 to 8% w/w of glycerin, 0.005 to 1% w/w of disodium EDTA, 0.005 to 1% w/w of benzophenone-4, 1 to 10% w/w of butylene glycol, 0.01 to 1% w/w of triethanolamine, 0.01 to 3% w/w of bis-PEG-18 methyl ether dimethyl silane, 0.01 to 1% w/w of xanthan gum, 0.01 to 5% w/w of c-isostearyl alcohol, and/or 1 to 10% w/w of diisostearyl malate. In some instances, the composition contains one or more of bis-PEG-18 methyl ether dimethyl silane and xanthan gum. In some instances, the composition contains 0.01 to 3% w/w of bis-PEG-18 methyl ether dimethyl silane and 0.01 to 1% w/w of xanthan gum. In some instances, the composition contains c-isostearyl alcohol. In some instances, the composition contains 0.01 to 5% w/w of c-isostearyl alcohol. In some instances, the composition contains diisostearyl malate. In some instances, the composition contains 1 to 10% w/w of diisostearyl malate.

In some aspects, the compositions of the present invention can further include a surfactant, a silicone containing compounds, a UV agent, an oil, and/or other ingredients identified in this specification or those known in the art. The composition can be a lotion, cream, body butter, mask, scrub, wash, gel, serum, emulsion (e.g., oil-in-water, water-in-oil, silicone-in-water, water-in-silicone, water-in-oil-in-water, oil-in-water-in-oil, oil-in-water-in-silicone, etc.), solutions (e.g., aqueous or hydro-alcoholic solutions), anhydrous bases (e.g., lipstick or a powder), ointments, milk, paste, aerosol, solid forms, eye jellies, gel serums, gel emulsions, etc. The composition can be formulated for topical skin application at least 1, 2, 3, 4, 5, 6, 7, or more times a day during use. In some aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, cps, etc., as measured on a Brookfield Viscometer using a TC spindle at 2.5 rpm at 25° C.).

The compositions, in non-limiting aspects, can have a pH of about 6 to about 9. In some aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride (e.g., caprylic capric triglyceride). The compositions can also include preservatives. Non-limiting examples of preservatives include phenoxyethanol, methylparaben, propylparaben, or any mixture thereof. In some embodiments, the composition is paraben-free.

Compositions of the present invention can have UVA and UVB absorption properties. The compositions can have an sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, or creams.

The compositions of the present invention can also include any one of, any combination of, or all of the following additional ingredients: a conditioning agent, a moisturizing agent, a pH adjuster, a structuring agent, inorganic salts, a preservative, a thickening agent, a silicone containing compound, an essential oil, a fragrance, a vitamin, a pharmaceutical ingredient, or an antioxidant, or any combination of such ingredients or mixtures of such ingredients. In certain aspects, the composition can include at least two, three, four, five, six, seven, eight, nine, ten, or more, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

Methods of use for the compositions disclosed herein are also disclosed. In some aspects, a method is disclosed to reduce the appearance of fine lines and wrinkles, moisturize skin, promote hydration, strengthen and repair skin, and/or firm and condition skin. In some aspects, a method is disclosed to increase skin moisturization, improve skin barrier function, reduce skin desquamation, reduce skin roughness, and increase skin lubricity. In some instances, the method comprises topically applying any one of the compositions disclosed herein to skin and/or the face and/or eye area in need thereof. In one aspect, any one of the compositions disclosed herein are topically applied and the composition is left on the application area, removed from the application area after a period of time, and/or removed directly after application.

In some aspects, the compositions disclosed herein are used to reduce the appearance of fine lines and wrinkles. In some aspects, the compositions disclosed herein are used to moisturize skin. In some aspects, the compositions disclosed herein are used to promote skin hydration. In some aspects, the compositions disclosed herein are used to strengthen and repair skin. In some aspects, the compositions disclosed herein are used to firm and condition skin. In some instances, the compositions disclosed herein are used to increase expression of hyaluronic acid. In some instances, the compositions disclosed herein are used to increase synthesis of ceramides. In some instances, compositions disclosed herein are used to increase production of filaggrin. In some instances, compositions disclosed herein are used to increase conductance of skin. In some instances, compositions disclosed herein are used to increase production of occludin. In some instances, compositions disclosed herein are used to inhibit TNFα production. In some instances, compositions disclosed herein are used to reduce oxidants. In some instances, the compositions disclosed herein are used to increase skin moisturization, improve skin barrier function, reduce skin desquamation, reduce skin roughness, and increase skin lubricity. In some instances, the methods disclosed herein comprise topically applying any one of the composition disclosed herein to skin and/or the face and/or eye area.

It is also contemplated that the compositions disclosed throughout this specification can be used as a leave-on or rinse-off composition. By way of example, a leave-on composition can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or overnight or throughout the day). Alternatively, a rinse-off composition can be a product that is intended to be applied to the skin and then removed or rinsed from the skin (e.g., with water) within a period of time such as less than 5, 4, 3, 2, or 1 minute. An example of a rinse off composition can be a skin cleanser, shampoo, conditioner, or soap. An example of a leave-on composition can be a skin moisturizer, sunscreen, mask, overnight cream, or a day cream.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, mist, dollop, or liquid. The container can include indicia on its surface. The indicia can be a word, an abbreviation, a picture, or a symbol.

It is contemplated that any embodiment discussed in this specification can be implemented with respect to any method or composition of the invention, and vice versa. Furthermore, compositions of the invention can be used to achieve methods of the invention.

In some embodiments, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a serum, a gel, a wash, a body butter, a scrub, a foundation, a night cream, a lipstick, a cleanser, a toner, a sunscreen, a mask, an anti-aging product, a deodorant, an antiperspirant, a perfume, a cologne, etc.

Also disclosed are the following Embodiments 1 to 30 of the present invention. Embodiment 1 is a method of treating skin comprising topically applying to the skin a topical composition comprising saccharide isomerate, sodium carrageenan, sea salt, and sodium hyaluronate. Embodiment 2 is the method of Embodiment 1, wherein the composition comprises 0.001 to 5% w/w of saccharide isomerate, 0.001 to 5% w/w of sodium carrageenan, 0.0001 to 5% w/w of sea salt, and 0.0001 to 1% w/w of sodium hyaluronate. Embodiment 3 is the method of any of Embodiments 1 to 2, wherein the composition comprises an amount of saccharide isomerate, sodium carrageenan, and sea salt effective to reduce the appearance of fine lines and wrinkles, moisturize skin, promote hydration, strengthen and repair skin, reduce inflammation and redness, reduce oxidizing agents, reduce skin desquamation, reduce skin roughness, increase skin lubricity, improve skin barrier function, and/or firm and condition skin. Embodiment 4 is the method of any of Embodiments 1 to 3, wherein the composition comprises an effective amount of sodium hyaluronate to increase skin moisturization, improve skin barrier function, reduce skin desquamation, reduce skin roughness, increase skin lubricity, and/or firm and condition skin. Embodiment 5 is the method of any of Embodiments 1 to 4, wherein the composition comprises: an effective amount of saccharide isomerate to condition and moisturize the skin, decrease TNF-α production, increase skin conductance, and/or increase antioxidant capacity; and/or an effective amount of sodium carrageenan and sea salt to promote hydration of the skin and strengthen and repair skin, increase epidermal and dermal production of hyaluronic acid, and/or increase stratum corneum and epidermal production of ceramides. Embodiment 6 is the method of any of Embodiments 1 to 5, wherein the composition comprises water. Embodiment 7 is the method of Embodiment 6, wherein the composition comprises 75 to 95% w/w of water. Embodiment 8 is the method of any of Embodiments 1 to 7, wherein the composition comprises glycerin, disodium EDTA, benzophenone-4, butylene glycol, and triethanolamine. Embodiment 9 is the method of Embodiment 8, wherein the composition comprises 0.5 to 8% w/w of glycerin, 0.005 to 1% w/w of disodium EDTA, 0.005 to 1% w/w of benzophenone-4, 1 to 10% w/w of butylene glycol, and 0.01 to 1% w/w of triethanolamine. Embodiment 10 is the method of any of Embodiments 1 to 9, wherein the composition comprises bis-PEG-18 methyl ether dimethyl silane and xanthan gum. Embodiment 11 is the method of Embodiment 10, wherein the composition comprises 0.01 to 3% w/w of bis-PEG-18 methyl ether dimethyl silane and 0.01 to 1% w/w of xanthan gum. Embodiment 12 is the method of any of Embodiments 1 to 11, wherein the composition comprises c-isostearyl alcohol. Embodiment 13 is the method of Embodiment 12, wherein the composition comprises 0.01 to 5% w/w of c-isostearyl alcohol. Embodiment 14 is the method of any of Embodiments 1 to 13, wherein the composition comprises diisostearyl malate. Embodiment 15 is the method of Embodiment 14, wherein the composition comprises 1 to 10% w/w of diisostearyl malate. Embodiment 16 is a topical composition comprising saccharide isomerate, sodium carrageenan, sea salt, and sodium hyaluronate. Embodiment 17 is the composition of Embodiment 16, wherein the composition comprises 0.001 to 5% w/w of saccharide isomerate, 0.001 to 5% w/w of sodium carrageenan, 0.0001 to 5% w/w of sea salt, and 0.0001 to 1% w/w of sodium hyaluronate. Embodiment 18 is the composition of any of Embodiments 16 to 17, wherein the composition comprises an amount of saccharide isomerate, sodium carrageenan, and sea salt effective to reduce the appearance of fine lines and wrinkles, moisturize skin, promote hydration, strengthen and repair skin, reduce inflammation and redness, reduce oxidizing agents, reduce skin desquamation, reduce skin roughness, increase skin lubricity, improve skin barrier function, and/or firm and condition skin. Embodiment 19 is the composition of any of Embodiments 16 to 18, wherein the composition comprises an effective amount of sodium hyaluronate to increase skin moisturization, improve skin barrier function, reduce skin desquamation, reduce skin roughness, increase skin lubricity, and/or firm and condition skin. Embodiment 20 is the composition of any of Embodiments 16 to 19, wherein the composition comprises an effective amount of saccharide isomerate to condition and moisturize the skin, decrease TNF-α production, increase skin conductance, and/or increase antioxidant capacity; and/or an effective amount of sodium carrageenan and sea salt to promote hydration of the skin and strengthen and repair skin, increase epidermal and dermal production of hyaluronic acid, and/or increase stratum corneum and epidermal production of ceramides. Embodiment 21 is the composition of any of Embodiments 16 to 20, wherein the composition comprises water. Embodiment 22 is the composition of Embodiment 21, wherein the composition comprises 75 to 95% w/w of water. Embodiment 23 is the composition of any of Embodiments 16 to 22, wherein the composition comprises glycerin, disodium EDTA, benzophenone-4, butylene glycol, and triethanolamine. Embodiment 24 is the composition of Embodiment 23, wherein the composition comprises 0.5 to 8% w/w of glycerin, 0.005 to 1% w/w of disodium EDTA, 0.005 to 1% w/w of benzophenone-4, 1 to 10% w/w of butylene glycol, and 0.01 to 1% w/w of triethanolamine. Embodiment 25 is the composition of any of Embodiments 16 to 24, wherein the composition comprises bis-PEG-18 methyl ether dimethyl silane and xanthan gum. Embodiment 26 is the composition of Embodiment 25, wherein the composition comprises 0.01 to 3% w/w of bis-PEG-18 methyl ether dimethyl silane and 0.01 to 1% w/w of xanthan gum. Embodiment 27 is the composition of any of Embodiments 16 to 26, wherein the composition comprises c-isostearyl alcohol. Embodiment 28 is the composition of Embodiment 27, wherein the composition comprises 0.01 to 5% w/w of c-isostearyl alcohol. Embodiment 29 is the composition of any of Embodiments 16 to 28, wherein the composition comprises diisostearyl malate. Embodiment 30 is the composition of Embodiment 29, wherein the composition comprises 1 to 10% w/w of diisostearyl malate.

"Topical application" means to apply or spread a composition onto the surface of lips or keratinous tissue. "Topical skin composition" includes compositions suitable for topical application on skin and/or keratinous tissue. Such compositions are typically dermatologically-acceptable in that they do not have undue toxicity, incompatibility, instability, allergic response, and the like, when applied to skin and/or keratinous tissue. Topical skin care compositions of the present invention can have a selected viscosity to avoid significant dripping or pooling after application to skin and/or keratinous tissue.

"Keratinous tissue" includes keratin-containing layers disposed as the outermost protective covering of mammals and includes, but is not limited to, lips, skin, hair, and nails.

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations are refers to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase, such as a measurable increase of a protein or molecule (e.g., matrix proteins such as fibronectin, laminin, collagen, or elastin or molecules such as hyaluronic acid) to achieve a desired result.

The term "effective," as that term is used in the specification and/or claims, means adequate to accomplish a desired, expected, or intended result.

The use of the word "a" or "an" when used in conjunction with the terms "comprising," "including," "having," or "containing," or any variations of these terms, in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the phrase "consisting essentially of," a basic and novel property of the compositions and methods of the present invention is the ability to reduce the appearance of fine lines and wrinkles, moisturize skin, promote hydration, strengthen and repair skin, firm and condition skin, improve skin barrier function, reduce skin desquamation, reduce skin roughness, and increase skin lubricity.

Other objects, features, and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1A:
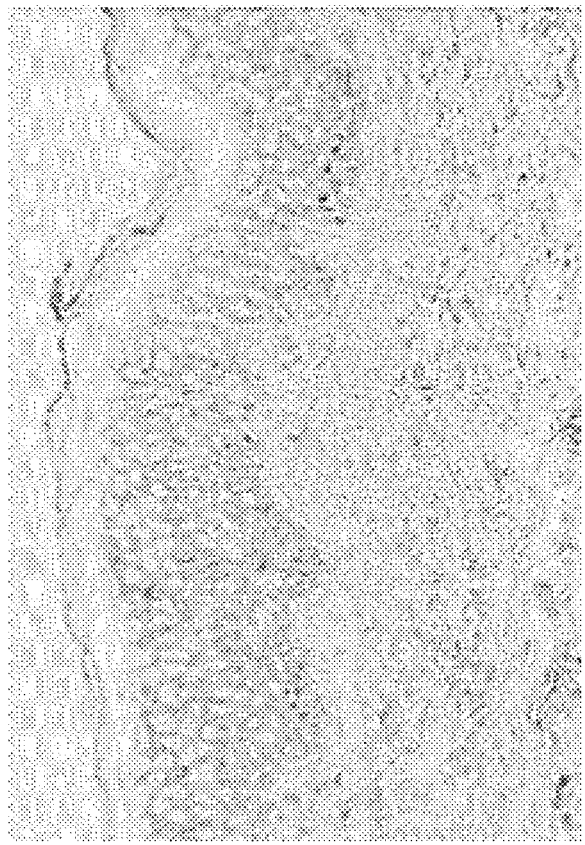
FIG. 1A is a histological view of hyaluronic acid (darker) in a human skin explant untreated control at Day 9.

As noted above, the present invention provides a solution to the problems associated with current cosmetic products. The solution is premised on the use of a combination of ingredients to reduce the appearance of fine lines and wrinkles, moisturize the skin, promote hydration, strengthen and repair skin, reduce inflammation and redness, reduce oxidizing agents, protect against pollution, improve skin barrier function, reduce skin desquamation, reduce skin roughness, increase skin lubricity, increase keratinocyte production of filaggrin and occludin, decrease TNF-α production, increase skin conductance, increase antioxidant capacity, increase epidermal and dermal production of hyaluronic acid, increase stratum corneum and epidermal production of ceramides, and/or firm and condition skin. A combination of saccharide isomerate (plankton extract), sodium carrageenan, sea salt, and sodium hyaluronate can be used to create the topical skin compositions.

The following subsections describe non-limiting aspects of the present invention in further detail.

A particular composition of the present invention is designed to work as a topical composition. The composition relies on a unique combination of any one of, any combination of, or all of saccharide isomerate, sodium carrageenan, sea salt, and sodium hyaluronate. These combinations can be used to create topical skin compositions that reduce the appearance of fine lines and wrinkles, moisturize skin, promote hydration, strengthen and repair skin, reduce oxidizing agents, protect against pollution, improve skin barrier function, reduce skin desquamation, reduce skin roughness, increase skin lubricity, and/or firm and condition skin. Non-limiting examples of such compositions are provided in Tables 3 to 9 of Example 3 below.

Some compositions disclosed herein can be applied to the skin and remain on the skin for a period of time (e.g., at least 1, 2, 3, 4, 5, 10, 20, 30, or 60 minutes or more). After which, the composition, if needed, can be rinsed from the skin or peeled from the skin. Some compositions disclosed herein can be applied to the skin and immediately rinsed from the skin. Some compositions disclosed herein can be applied to the skin and absorbed at least in part by the skin.

These and other non-limiting aspects of the present invention are described in the following sections.

A. Active Ingredients

The present invention is premised on a determination that a combination of one or more of active ingredients—saccharide isomerate, sodium carrageenan, sodium hyaluronate, and sea salt—can be used to reduce the appearance of fine lines and wrinkles.

Saccharide isomerate is an exopolysaccharide synthesized by a micro-organism called *Vibrio alginolyticus* and belonging to the family of Thalasso plankton. In some instances, this ingredient is commercially available, e.g., from Barnet, which provides saccharide isomerate under the trade name Benoiderm. It has been determined that this ingredient can be used to increase production of filaggrin, increase skin moisture, increase production of occluding, inhibit TNFα production, and reduce oxidants.

Sodium carrageenan is the sodium salt of carrageenan, a polysaccharide extracted from various members of the Gigartinaceae or Solieriaceae families of the red seaweed, Rhodophyceae. Sea salt is salt produced from the evaporation of seawater, rather than by extraction from sedimentary deposits. It has been determined that a combination of sea salt and sodium carrageenan can be used to increase production of hyaluronic acid and ceramides in skin. In some instances, sea salt is commercially available in combination with sodium carrageenan. In some instances, this ingredient is commercially available, e.g., from Barnet, which provides a combination of sodium carrageenan and sea salt under the trade name AESTHIGEL™.

Sodium hyaluronate is the sodium salt of hyaluronic acid, a compound that occurs naturally in various tissues including connective tissue. In some instances, sodium hyaluronate is commercially available in powder form, e.g., from Tri-K Industries under the trade name HyaClear® Solution, and has been shown to increase skin moisturization, improve skin barrier function, reduce skin desquamation, reduce skin roughness, and increase skin lubricity (HyaClear® Solution Presentation, Tri-K Industries, Inc., 2016).

This combination of ingredients can be used in different product forms to treat various skin conditions. By way of non-limiting examples, the combination of ingredients can be formulated in an emulsion (e.g., oil in water, water in oil), a gel, a serum, a gel emulsion, a gel serum, a lotion, a mask, a scrub, a wash, a cream, or a body butter.

The extracts described herein can be extracts made through extraction methods known in the art and combinations thereof. Non-limiting examples of extraction methods include the use of liquid-liquid extraction, solid phase extraction, aqueous extraction, ethyl acetate, alcohol, acetone, oil, supercritical carbon dioxide, heat, pressure, pressure drop extraction, ultrasonic extraction, etc. Extracts can be a liquid, solid, dried liquid, re-suspended solid, etc.

B. Amounts of Ingredients

It is contemplated that the compositions of the present invention can include any amount of the ingredients discussed in this specification. The compositions can also include any number of combinations of additional ingredients described throughout this specification (e.g., pigments, or additional cosmetic or pharmaceutical ingredients). The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

C. Vehicles

The compositions of the present invention can include or be incorporated into all types of vehicles and carriers. The vehicle or carrier can be a pharmaceutically or dermatologically acceptable vehicle or carrier. Non-limiting examples of vehicles or carriers include water, glycerin, alcohol, oil, a silicon containing compound, a silicone compound, and wax. Variations and other appropriate vehicles will be apparent to the skilled artisan and are appropriate for use in the present invention. In certain aspects, the concentrations and combinations of the compounds, ingredients, and agents can be selected in such a way that the combinations are chemically compatible and do not form complexes which precipitate from the finished product.

D. Structure

The compositions of the present invention can be structured or formulated into a variety of different forms. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, masks, scrubs, body butters, peels, and ointments. Variations and other structures will be apparent to the skilled artisan and are appropriate for use in the present invention.

E. Additional Ingredients

In addition to the combination of ingredients disclosed by the inventors, the compositions can also include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrance agents (artificial and natural; e.g., gluconic acid, phenoxyethanol, and triethanolamine), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), flavoring agents/aroma agents (e.g., *Stevia rebaudiana* (sweetleaf) extract, and menthol), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as para-aminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., *Aloe vera*, chamomile, cucumber extract, *Ginkgo biloba*, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, methyl gluceth-20, saccharide isomerate, and mannitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, biosaccharide gum-1, ethylhexylglycerin, pentylene glycol, hydrogenated polydecene, octyldodecyl oleate, and dipotassium glycyrrhizate). Non-limiting examples of some of these ingredients are provided in the following subsections.

a. UV Absorption and/or Reflecting Agents

UV absorption and/or reflecting agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate (octinoxate), isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrrolidone carboxylic acid, potassium PCA, propylene glycol, saccharide isomerate, sodium glucuronate, sodium PCA, sorbitol, sucrose, trehalose, urea, and xylitol.

Other examples include acetylated lanolin, acetylated lanolin alcohol, alanine, algae extract, *Aloe barbadensis*, *Aloe barbadensis* extract, *Aloe barbadensis* gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamom (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, Geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, *Macadamia ternifolia* nut oil, maltitol, matricaria (*Chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (Menthapiperita) oil, petrolatum, phospholipids, plankton extract, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (see U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds include silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Michigan. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Michigan.

g. Exfoliating Agent

Exfoliating agents include ingredients that remove dead skin cells on the skin's outer surface. These agents may act through mechanical, chemical, and/or other means. Non-limiting examples of mechanical exfoliating agents include abrasives such as pumice, silica, cloth, paper, shells, beads, solid crystals, solid polymers, etc. Non-limiting examples of chemical exfoliating agents include acids and enzyme exfoliants. Acids that can be used as exfoliating agents include, but are not limited to, glycolic acid, lactic acid, citric acid, alpha hydroxy acids, beta hydroxy acids, etc. Other exfoliating agents known to those of skill in the art are also contemplated as being useful within the context of the present invention.

h. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang-ylang. Other essential oils known to those of skill in the art are also contemplated as being useful within the context of the present invention.

i. Thickening Agents

Thickening agents, including thickener or gelling agents, include substances which that can increase the viscosity of a composition. Thickeners include those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyltaurate/VP copolymer, or a mixture of them.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerythritol (e.g., CARBOPOL™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three units.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

j. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

F. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Materials Used

The active ingredients in Table 1 were used to obtain the in vitro data noted below.

TABLE 1

| Ingredient |
|---|
| Saccharide isomerate, supplied by Barnet under the tradename Benoiderm. |
| Water and sodium carrageenan and sea salt, supplied by Barnet under the tradename AESTHIGEL ™. |
| Sodium hyaluronate, supplied by Tri-K Industries. |

Example 2

In-Vitro Activities

It has been determined that saccharide isomerate, sodium carrageenan, sodium hyaluronate, and sea salt can reduce the appearance of fine lines and wrinkles, moisturize skin, promote hydration, strengthen and repair skin, reduce oxidizing agents, protect against pollution, and/or firm and condition skin. A summary of results are found in Table 2 and the methods used to determine the properties of the ingredients are provided below.

TABLE 2

| Ingredient | Assay | Activity |
|---|---|---|
| Saccharide isomerate | Keratinocyte Production of Filaggrin | +28% |
| | Artificial Skin Moisturization/Hydration | +79% |
| | Keratinocyte Production of Occludin | +170% |
| | Keratinocyte Production of TNF-α | −88% |
| | Antioxidant Capacity | +36% |
| Sodium carrageenan and sea salts (AESTHIGEL ™) | Epidermal Production of Hyaluronic Acid | +210% |
| | Dermal Production of Hyaluronic Acid | +124% |
| | Stratum Corneum Production of Ceramides | +51% |
| | Epidermal Production of Ceramides | +55% |

Production of Filaggrin:

Changes in the production of filaggrin in keratinocytes due to saccharide isomerate were measured. Filaggrin is a precursor to Natural Moisturizing Factor (NMF) in the skin. Increased NMF increases the moisture content of the skin. It was determined that saccharide isomerate increased keratinocyte production of filaggrin by 28%.

Filaggrin production in treated and non-treated keratinocytes were determined using a bioassay that analyzes filaggrin concentration in keratinocyte cell lysates. As a non-limiting example, the bioassay was performed using the PROTEINSIMPLE® SIMONE™ western blotting protocol. The PROTEINSIMPLE® SIMON™ western blotting bioassay employs a quantitative western blotting immunoassay technique using an antibody specific for filaggrin to quantitatively detect filaggrin in the test samples. For each sample, normal human epidermal keratinocytes (NHEK) were grown in EPI-200-Mattek EPILIFE® growth media with calcium from Life Technologies (M-EP-500-CA). NHEK were incubated in growth medium overnight at 37° C. in 5% $CO_2$ prior to treatment. NHEK were then incubated in growth medium with saccharide isomerate or no saccharide isomerate (negative control) for 24 to 36 hours. The NHEK were then washed, collected, and stored on ice or colder until lysed on ice using a lysis buffer and sonication. The lysates were stored at −80° C. until use in the quantification assay.

After lysing, cell samples were normalized for protein concentration. Normalized samples and molecular weight standards were then loaded and ran on a denatured protein separation gel using capillary electrophoresis. The proteins in the gel were immobilized and immunoprobed using a primary antibody specific for filaggrin. The immobilized proteins were then immunoprobed with an enzyme-linked detection antibody that binds the primary antibody. A chemiluminescent substrate solution was then added to the immobilized proteins to allow chemiluminescent development in proportion to the amount of filaggrin bound in the immobilization. The chemiluminescent development was stopped at a specific time and the intensity of the chemiluminescent signal was then measured and compared to positive and negative controls.

Skin Moisturization/Hydration:

Saccharide isomerate was shown to increase a clinical measurement of skin moisturization using a skin moisture/hydration assay. This assay determined impedance measurements with the Nova Dermal Phase Meter. The impedance meter measured changes in skin moisture content. The outer layer of the skin has distinct electrical properties. When skin is dry it conducts electricity very poorly. As it becomes more hydrated increasing conductivity results. Consequently, changes in skin impedance (related to conductivity) were used to assess changes in skin hydration. It was determined that saccharide isomerate increased conductance by 79%, indicating increased moisture/hydration.

For this assay, treated and non-treated artificial skin equivalents were used. The Nova Dermal Phase Meter was calibrated according to instrument instructions for each testing day. A notation of temperature and relative humidity was made for comparison purposes. Impedance was evaluated as follows: prior to measurement, the samples were equilibrated in a room with defined humidity (e.g., 30-50%) and temperature (e.g., 68-72° C.). Impedance readings were taken on each sample, recorded, and averaged. The T5 setting was used on the impedance meter which averages the impedance values of every five seconds after application to the sample. Changes were reported with statistical variance and significance.

Production of Occludin:

Occludin is a protein critical to the formation of tight junctions and the skin's moisture barrier function. It was determined that saccharide isomerate increased keratinocyte production of occludin by 170%.

Occludin production in treated and non-treated keratinocytes was determined using a bioassay that analyzed occludin concentration in keratinocyte cell lysates. As a non-limiting example, the bioassay was performed using the PROTEINSIMPLE® SIMON™ western blotting protocol. The bioassay employed a quantitative western blotting immunoassay technique using an antibody specific for occludin to quantitatively detect occludin in the test samples. For the samples, adult human epidermal keratinocytes (HEKa) from Life Technologies (C-005-5C) were grown at 37° C. and 5% C02 for 24 hours in EPILIFE® growth media with calcium from Life Technologies (M-EP-500-CA) supplemented with Keratinocyte Growth Supplement (HKGS) from Life Technologies (S-101-5). HEKa were then incubated in growth medium with saccharide isomerate, no saccharide isomerate for negative control, or with 1 mM $CaCl_2$ for positive control for 24 to 48 hours. The HEKa were then washed, collected, and stored on ice or colder until lysed on ice using a lysis buffer and sonication. The protein concentrations of the samples were determined and used to normalize the samples. The lysates were stored at −80° C. until use in the bioassay.

Cell samples were lysed and normalized for protein concentration. Normalized samples and molecular weight standards were then loaded and ran on a denatured protein separation gel using capillary electrophoresis. The proteins in the gel were immobilized and immunoprobed using a primary antibody specific for occludin. The immobilized proteins were then immunoprobed with an enzyme-linked detection antibody that binds the primary antibody. A chemiluminescent substrate solution was then added to the immobilized proteins to allow chemiluminescent development in proportion to the amount of occludin bound in the immobilization. The chemiluminescent development was stopped at a specific time and the intensity of the chemiluminescent signal was measured and compared to positive and negative controls.

Inhibition of Tumor Necrosis Factor Alpha (TNF-α):

Saccharide isomerate was shown to inhibit TNF-α production in keratinocytes. TNF-α is the prototype ligand of the TNF superfamily. It is a pleiotropic cytokine that plays a central role in inflammation. Increase in its expression is associated with an upregulation in pro-inflammatory activity. The bioassay used to analyze the effect of saccharide isomerate used a spectrophotometric measurement that reflects the presence of TNF-α and cellular viability. It was determined that saccharide isomerate inhibits TNF-α production in keratinocytes by 88%.

Subconfluent normal human adult keratinocytes (Cascade Biologics) cultivated in EpiLife standard growth medium (Cascade Biologics) at 37° C. in 5% CO2, were treated with phorbol 12-myristate 13-acetate (PMA, 10 ng/ml, Sigma Chemical, #P1585-1MG) and either saccharide isomerate (treated sample) or no additional treatment (untreated sample) for 6 hours. PMA caused a dramatic increase in TNF-α secretion which peaked at 6 hours after treatment. Following incubation, cell culture medium was collected and the amount of TNF-α secretion quantified using a sandwich enzyme linked immunosorbent assay (ELISA) from R&D Systems (#DTA00C).

Briefly, the ELISA assay employed the quantitative sandwich enzyme immunoassay technique whereby a monoclonal antibody specific for TNF-α was pre-coated onto a microplate. Standards and treated and untreated samples were pipetted into the microplate wells to allow any TNF-α present to be bound by the immobilized antibody. After washing away any unbound substances, an enzyme-linked polyclonal antibody specific for TNF-α was added to the wells. Following a wash to remove any unbound antibody-enzyme reagent, a substrate solution was added to the wells to allow color development in proportion to the amount of TNF-α bound in the initial step. The color development was stopped at a specific time and the intensity of the color at 450 nm was measured using a microplate reader.

Antioxidant Capacity:

Saccharide isomerate was shown to possess antioxidant capacity. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it accounts for the cumulative effect of all antioxidants present in plasma and body fluids. It was determined that saccharide isomerate possesses an antioxidant capacity of 36% of trolox, which indicates that saccharide isomerate is capable of reducing oxidizing agents (oxidants).

Antioxidant capacity was determined by an Oxygen Radical Absorption (or Absorbance) Capacity (ORAC) assay. This assay quantifies the degree and length of time it takes to inhibit the action of an oxidizing agent, such as oxygen radicals, that are known to cause damage to cells (e.g., skin cells). The ORAC value of control and saccharide isomerate was determined by the Zen-Bio ORAC Anti-oxidant Assay kit (#AOX-2). Briefly, this assay measures the loss of fluorescein fluorescence over time due to the peroxyl-radical formation by the breakdown of AAPH (2,2'-axobis-2-methyl propanimidamide, dihydrochloride). Trolox, a water soluble vitamin E analog, serves as positive control inhibition fluorescein decay in a dose dependent manner.

Production of Hyaluronic Acid:

AESTHIGEL™ (sodium carrageenan and sea salt) was tested at 1.5% in water (i.e., 0.00975% of dry matter). Human skin explants with a diameter of about 11 mm were taken from an abdominoplasty of a woman aged 50 years.

The explants were cultured in survival explants medium at 37° C. in a humidified atmosphere supplemented with 5% CO2. The treatment was carried out by topical application of 2 mg of product per explant (n=3) using a small spatula on days D0, D2, D3, D6, D8, and D9. The control explants (n=3) received no treatment except renewal of survival explants medium. The survival medium was renewed for half (1 mL) to J3, J6, and J8. At D9, three explants of each condition were taken and cut in half. A half explant was fixed in buffered formalin and the other was frozen at −80° C.

After 48 hours of fixation in ordinary Bouin and 24 hours in formalin, the samples were dried and soaked in paraffin using an automatic tissue processor Leica TP 1020. Sections of 5 microns were performed with a microtome (Minot type Leica RM2125) and mounted on Superfrost™ histological slides. Microscopic observations were performed by optical microscopy, using a Leica Orthoplan or Leica DM LB microscope. The images taken were made with an Olympus DP72 camera and Cell^D software. The general morphology was examined on paraffin sections stained with Masson's trichrome Goldner variant. The staining of hyaluronic acid was performed with an anti-hyaluronic acid biotinylated protein (HABP) (Seikagaku ref 400763-1A) diluted to 1/100 for 1 hour at room temperature, with an amplifier system biotin/streptavidin (Vector, Vectastain PK-7200).

Figure 1B:
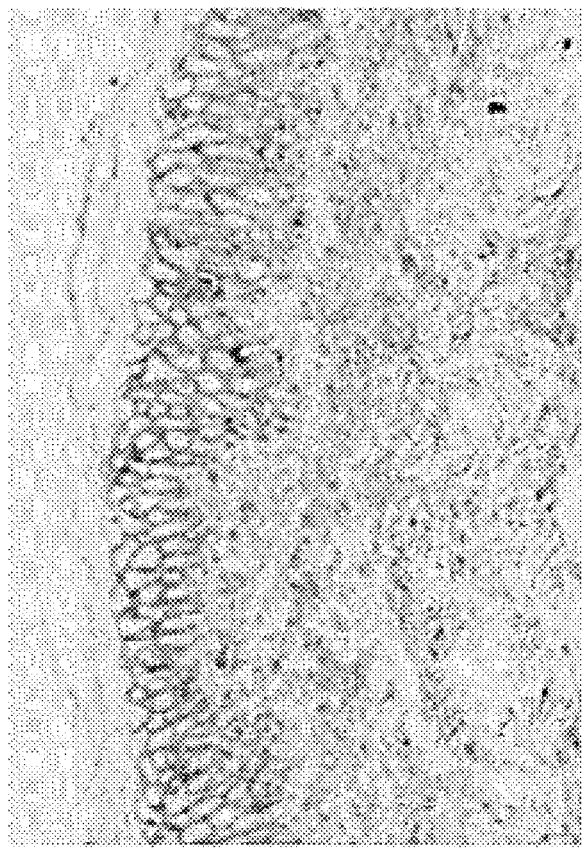
FIG. 1B is a histological view of hyaluronic acid (darker) in a human skin explant at Day 9 that was treated with sodium carrageenan and sea salt.
Figure 2:
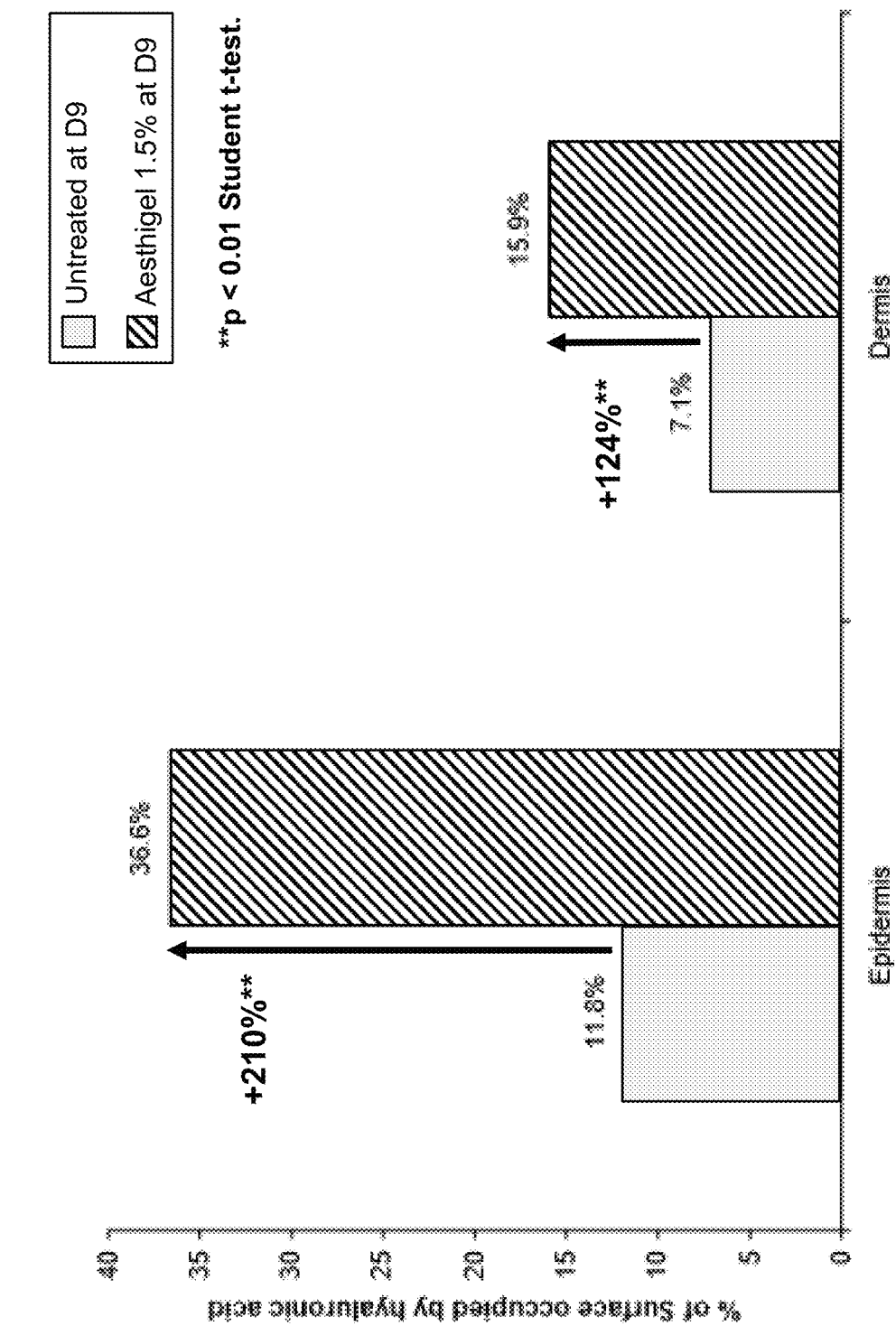
FIG. 2 is a chart showing the effect of sodium carrageenan and sea salt on hyaluronic acid synthesis in epidermis and dermis, as compared to untreated explants.

Referring to FIGS. 1A-1B, histological images of explanted tissue at D9 are depicted, with the untreated control (FIG. 1A) on the left and the sodium carrageenan and sea salt treated sample (FIG. 1B) on the right showing increase in hyaluronic acid synthesis (darker stain). Referring to FIG. 2, the effect of sodium carrageenan and sea salt on hyaluronic acid synthesis in epidermis and dermis is shown in comparison with untreated explants. The Student t-test was used to determine the probability for the two batches to be statistically significant. The difference between two groups is significant if $p<0.1$ (#), a 90% probability for two batches to be significantly different or $p<0.05$ (*), a 95% probability for two batch to be significantly different or $p<0.01$ (**), a 99% probability for two batch to be significantly different. Hyaluronic acid in the untreated explants occupied 11.8% of the total surface area of the epidermis, as compared to 36.6% of the epidermal surface in explants treated with sodium carrageenan and sea salt. Hyaluronic acid in the untreated explants occupied 7.1% of the total surface area of the dermis, as compared to 15.9% of the dermal surface in explants treated with sodium carrageenan and sea salt. In this statistically significant comparison study ($p<0.01$), sodium carrageenan and sea salt therefore significantly increased the synthesis of hyaluronic acid production by 210% in the epidermis and by 124% in the dermis.

Production of Ceramides:

Ceramides were labeled with a mouse monoclonal antibody anti-ceramide (Enzo Life Science, ref ALX-804-196 clone MID15B4) diluted to 1/50 for 2 hours at room temperature with an amplifier system biotin/streptavidin. Video microscope observation was performed to view ceramides (pink stain).

Figure 3B:
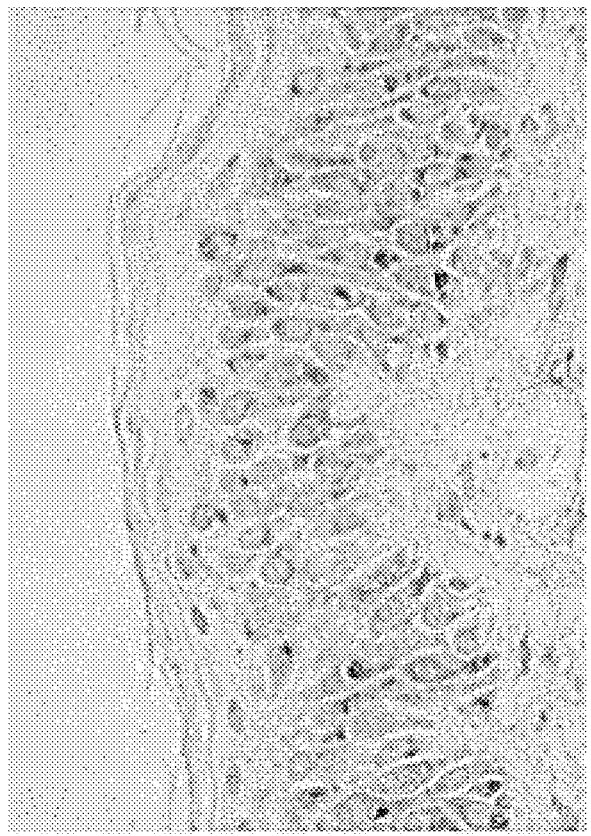
FIG. 3B is a histological view of ceramides (darker) in a human skin explant at Day 9 that was treated with sodium carrageenan and sea salt.
Figure 3A:
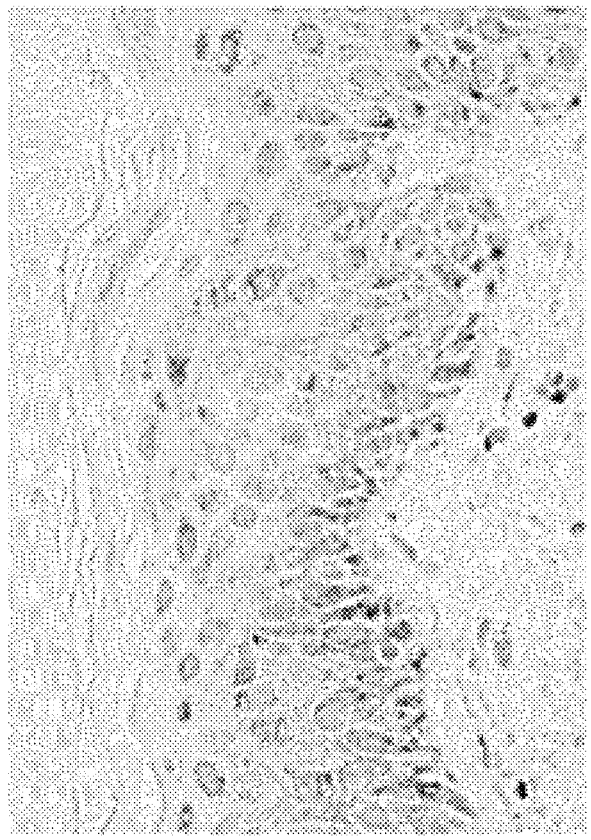
FIG. 3A is a histological view of ceramides (darker) in a human skin explant untreated control at Day 9.
Figure 4:
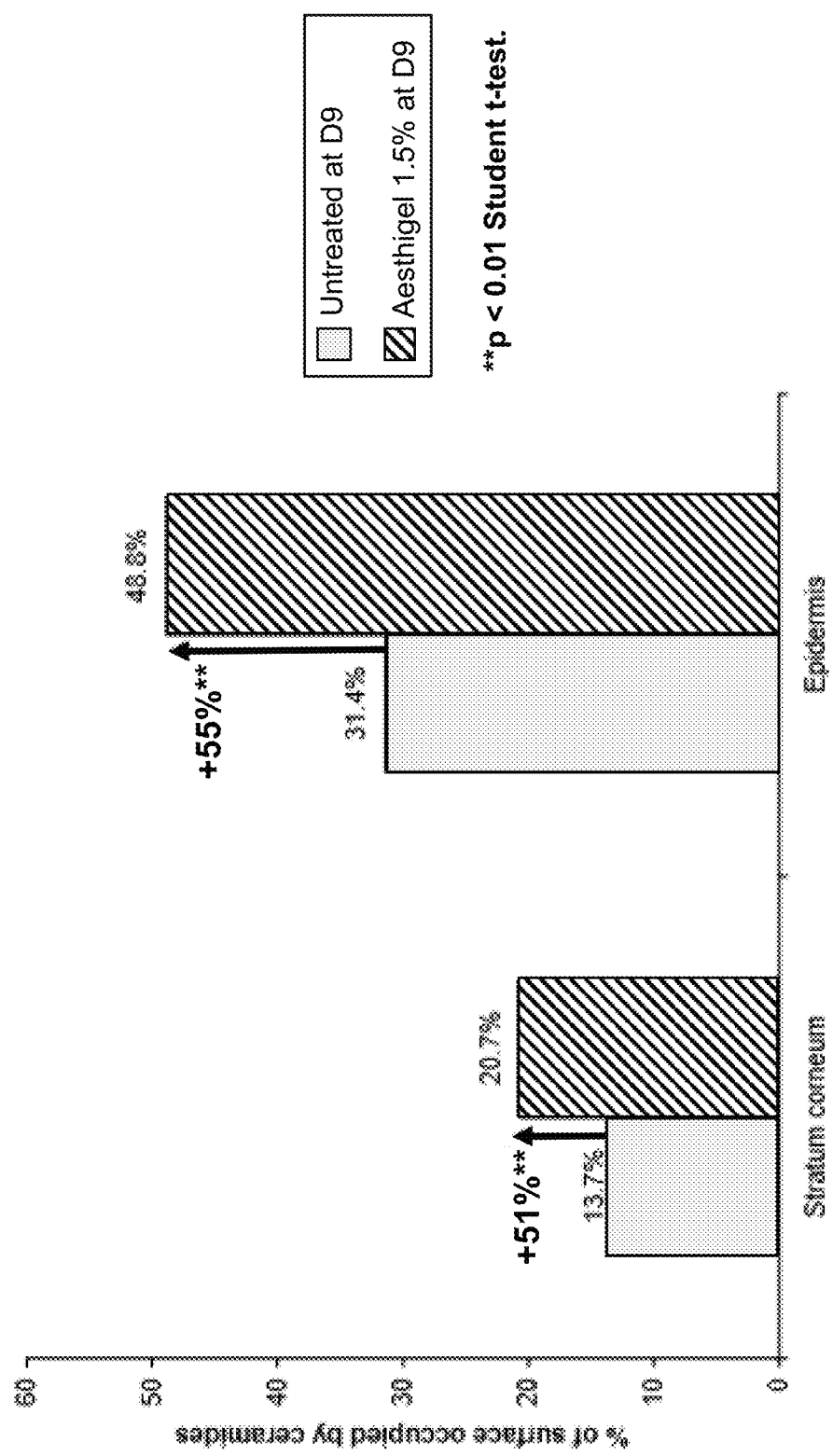
FIG. 4 is a chart showing the effect of sodium carrageenan and sea salt on ceramide synthesis in the stratum corneum and epidermis, as compared to an untreated explants.

Referring to FIGS. 3A-3B, histological images of explanted tissue at D9 are depicted, with the untreated control (FIG. 3A) on the left and the sodium carrageenan and sea salt treated sample (FIG. 3B) on the right showing increase in ceramide synthesis (darker stain). Referring to FIG. 4, the effect of sodium carrageenan and sea salt on ceramide synthesis in stratum corneum and epidermis is shown in comparison with untreated explants. The Student t-test was used to determine the probability for the two batches to be statistically significant. The difference between two groups is significant if $p<0.1$ (#), a 90% probability for two batches to be significantly different or $p<0.05$ (*), a 95% probability for two batch to be significantly different or $p<0.01$ (**), a 99% probability for two batch to be significantly different. Ceramides in the untreated explants occupied 13.7% of the total surface of the stratum corneum, as compared to 20.7% of the stratum corneum surface in explants treated with sodium carrageenan and sea salt. Ceramides in the untreated explants occupied 31.4% of the total surface area of the epidermis, as compared to 48.8% of the epidermal surface in explants treated with sodium carrageenan and sea salt. In this statistically significant comparison study ($p<0.01$), sodium carrageenan and sea salt therefore significantly increased the synthesis of ceramides by 51% in the stratum corneum and by 55% in the epidermis.

Example 3

Exemplary Formulations

Formulations having the ingredients disclosed herein were prepared as topical skin compositions. The formulation in Table 3 is an example of a topical skin composition prepared as a serum.

TABLE 3^

| Ingredient | % Concentration (by weight) |
|---|---|
| Water | 90 |
| Pemulen ™ TR-2[1] | 0.1 |
| Carbopol ® Ultrez 10[2] | 0.2 |
| Disodium EDTA | 0.1 |
| Benzophenone-4 | 0.1 |
| Glycerin | 2.0 |
| Butylene glycol | 2.5 |
| Glycacil ® 2000[3] | 0.2 |
| Symdiol ® 68[4] | 0.5 |
| Actimoist ® Bio-1 PF[5] | 0.3 |
| Saccharide isomerate | 1.0 |
| Water and Sodium Carrageenan and Sea Salt | 1.5 |
| Bis-PEG-18 Methyl Ether Dimethyl Silane | 0.5 |
| Xanthan gum | 0.2 |
| Isostearyl alcohol | 0.8 |
| Triethanolamine | 0.3 |
| Excipients* | q.s. |

^The formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition or ingredients that provide benefits to skin.
[1]Pemulen ™ TR-2 comprises ethyl acetate and cyclohexane.
[2]Carbopol ® Ultrez 10 comprises carbomer.
[3]Glycacil ® 2000 comprises 3-iodo-2-propinylbutylcarbamate and cyclodextrin derivative.
[4]Symdiol ® 68 comprises 1,2-hexanediol and caprylyl glycol.
[5]Actimoist ® Bio-1 PF comprises sodium hyaluronate.
*Excipients can be added, for example, to modify the rheological properties of the composition. Alternatively, the amount of water can be varied so long as the amount of water in the composition is at least 40% w/w, and preferably between 60 to 98% w/w.

The formulation in Table 4 is another example of a topical skin composition prepared as a serum.

TABLE 4^

| Ingredient | % Concentration (by weight) |
|---|---|
| Water | 90 |
| Pemulen ™ TR-2[1] | 0.1 |
| Carbopol ® Ultrez 10[2] | 0.2 |
| Disodium EDTA | 0.1 |
| Benzophenone-4 | 0.1 |
| Glycerin | 2.0 |

TABLE 4ˆ-continued

| Ingredient | % Concentration (by weight) |
|---|---|
| Butylene glycol | 2.5 |
| Glycacil ® 2000[3] | 0.2 |
| Caprylyl Glycol and Phenoxyethanol | 0.8 |
| Actimoist ® Bio-1 PF[4] | 0.3 |
| Saccharide isomerate | 1.0 |
| Water and Sodium Carrageenan and Sea Salt | 1.5 |
| Bis-PEG-18 Methyl Ether Dimethyl Silane | 0.5 |
| Xanthan gum | 0.2 |
| Isostearyl alcohol | 0.8 |
| Triethanolamine | 0.3 |
| Excipients* | q.s. |

ˆThe formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition or ingredients that provide benefits to skin.
[1]Pemulen ™ TR-2 comprises ethyl acetate and cyclohexane.
[2]Carbopol ® Ultrez 10 comprises carbomer.
[3]Glycacil ® 2000 comprises 3-iodo-2-propinylbutylcarbamate and cyclodextrin derivative.
[4]Actimoist ® Bio-1 PF comprises sodium hyaluronate.
*Excipients can be added, for example, to modify the rheological properties of the composition. Alternatively, the amount of water can be varied so long as the amount of water in the composition is at least 40% w/w, and preferably between 60 to 98% w/w.

The formulation in Table 5 is another example of a topical skin composition prepared as a serum.

TABLE 5ˆ

| Ingredient | % Concentration (by weight) |
|---|---|
| Water | 91 |
| Carbopol ® Ultrez 10[1] | 0.2 |
| Disodium EDTA | 0.1 |
| Benzophenone-4 | 0.1 |
| Glycerin | 2.0 |
| Butylene glycol | 2.5 |
| Glycacil ® 2000[2] | 0.2 |
| Symdiol ® 68[3] | 0.5 |
| Actimoist ® Bio-1 PF[4] | 0.1 |
| Saccharide isomerate | 1.0 |
| Water and Sodium Carrageenan and Sea Salt | 1.5 |
| Bis-PEG-18 Methyl Ether Dimethyl Silane | 0.2 |
| Xanthan gum | 0.2 |
| Seric OMC[5] | 0.3 |
| Triethanolamine | 0.3 |
| Excipients* | q.s. |

ˆThe formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition or ingredients that provide benefits to skin.
[1]Carbopol ® Ultrez 10 comprises carbomer.
[2]Glycacil ® 2000 comprises 3-iodo-2-propinylbutylcarbamate and cyclodextrin derivative.
[3]Symdiol ® 68 comprises 1,2-hexanediol and caprylyl glycol.
[4]Actimoist ® Bio-1 PF comprises sodium hyaluronate.
[5]Seric OMC comprises mica, ethylhexyl methoxycinnamate, hydrogenated lecithin, and butylene glycol.
*Excipients can be added, for example, to modify the rheological properties of the composition. Alternatively, the amount of water can be varied so long as the amount of water in the composition is at least 40% w/w, and preferably between 60 to 98% w/w.

The formulation in Table 6 is another example of a topical skin composition prepared as a serum.

TABLE 6ˆ

| Ingredient | % Concentration (by weight) |
|---|---|
| Water | 93 |
| Carbomer | 0.2 |
| Disodium EDTA | 0.1 |
| Benzophenone-4 | 0.1 |
| Glycerin | 2.0 |
| Butylene glycol | 2.5 |
| Hydroxypropyl cyclodextrin | 0.1 |
| Iodopropynyl butylcarbamate | 0.01 |
| Caprylyl glycol | 0.3 |
| Sodium hyaluronate | 0.001 |
| Sodium benzoate | 0.0001 |
| Saccharide isomerate | 0.01 |
| Phenoxyethanol | 0.4 |
| Sodium Carrageenan | 0.01 |
| Sea salt | 0.0008 |
| Bis-PEG-18 Methyl Ether Dimethyl Silane | 0.2 |
| Xanthan gum | 0.2 |
| Seric OMC[2] | 0.3 |
| Triethanolamine | 0.3 |
| Excipients* | q.s. |

ˆThe formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition or ingredients that provide benefits to skin.
[2]Seric OMC comprises mica, ethylhexyl methoxycinnamate, hydrogenated lecithin, and butylene glycol.
*Excipients can be added, for example, to modify the rheological properties of the composition. Alternatively, the amount of water can be varied so long as the amount of water in the composition is at least 40% w/w, and preferably between 60 to 98% w/w.

The formulation in Table 7 is another example of a topical skin composition prepared as a serum.

TABLE 7ˆ

| Ingredient | % Concentration (by weight) |
|---|---|
| Water | 82 |
| Pemulen ™ TR-2[1] | 0.1 |
| Carbopol ® Ultrez 10[2] | 0.1 |
| Disodium EDTA | 0.1 |
| Benzophenone-4 | 0.1 |
| Bis-PEG-18 Methyl Ether Dimethyl Silane | 1.5 |
| Glycerin | 3.5 |
| Butylene glycol | 2.5 |
| Glycacil ® 2000[3] | 0.2 |
| Symdiol ® 68[4] | 0.5 |
| Actimoist ® Bio-1 PF[5] | 0.2 |
| Saccharide isomerate | 1.0 |
| Water and Sodium Carrageenan and Sea Salt | 1.5 |
| Diisostearyl malate | 3.9 |
| Xanthan gum | 0.2 |
| AMP-600 | 0.04 |
| Triethanolamine | 0.3 |
| Excipients* | q.s. |

ˆThe formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition or ingredients that provide benefits to skin.
[1]Pemulen ™ TR-2 comprises ethyl acetate and cyclohexane.
[2]Carbopol ® Ultrez 10 comprises carbomer.
[3]Glycacil ® 2000 comprises 3-iodo-2-propinylbutylcarbamate and cyclodextrin derivative.
[4]Symdiol ® 68 comprises 1,2-hexanediol and caprylyl glycol.
[5]Actimoist ® Bio-1 PF comprises sodium hyaluronate.
*Excipients can be added, for example, to modify the rheological properties of the composition. Alternatively, the amount of water can be varied so long as the amount of water in the composition is at least 40% w/w, and preferably between 60 to 95% w/w.

The formulation in Table 8 is another example of a topical skin composition prepared as a serum.

TABLE 8ˆ

| Ingredient | % Concentration (by weight) |
|---|---|
| Water | 82 |
| Pemulen ™ TR-2[1] | 0.1 |
| Carbopol ® Ultrez 10[2] | 0.1 |
| Disodium EDTA | 0.1 |
| Benzophenone-4 | 0.1 |
| Bis-PEG-18 Methyl Ether Dimethyl Silane | 1.5 |

TABLE 8^-continued

| Ingredient | % Concentration (by weight) |
|---|---|
| Glycerin | 3.5 |
| Butylene glycol | 2.5 |
| Glycacil ® 2000[3] | 0.2 |
| Caprylyl glycol and phenoxyethanol | 0.8 |
| Actimoist ® Bio-1 PF[4] | 0.2 |
| Saccharide isomerate | 1.0 |
| Water and Sodium Carrageenan and Sea Salt | 1.5 |
| Diisostearyl malate | 3.9 |
| Xanthan gum | 0.2 |
| AMP-600 | 0.04 |
| Triethanolamine | 0.3 |
| Excipients* | q.s. |

^The formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition or ingredients that provide benefits to skin.
[1]Pemulen ™ TR-2 comprises ethyl acetate and cyclohexane.
[2]Carbopol ® Ultrez 10 comprises carbomer.
[3]Glycacil ® 2000 comprises 3-iodo-2-propinylbutylcarbamate and cyclodextrin derivative.
[4]Actimoist ® Bio-1 PF comprises sodium hyaluronate.
*Excipients can be added, for example, to modify the rheological properties of the composition. Alternatively, the amount of water can be varied so long as the amount of water in the composition is at least 40% w/w, and preferably between 60 to 95% w/w.

The formulation in Table 9 is another example of a topical skin composition prepared as an eye gel.

TABLE 9^

| Ingredient | % Concentration (by weight) |
|---|---|
| Water | 88 |
| Butylene glycol | 5.0 |
| Glycerin | 4.1 |
| Hydroxyacetophenone | 0.5 |
| Pentylene glycol | 0.4 |
| Triethanolamine | 0.4 |
| Acrylates/C10-30 alkyl acrylate crosspolymer | 0.4 |
| Propanediol | 0.4 |
| Glyceryl acrylate/acrylic acid copolymer | 0.3 |
| Caprylyl glycol | 0.2 |
| Phenoxyethanol | 0.1 |
| Benzophenone-4 | 0.1 |
| Ethylhexylglycerin | 0.1 |
| Disodium EDTA | 0.1 |
| Propylene glycol | 0.01 |
| Saccharide isomerate | 0.01 |
| Sodium carrageenan | 0.01 |
| Sodium hyaluronate | 0.01 |
| Sea salt | 0.001 |
| Excipients* | q.s. |

^The formulation can be prepared by mixing the ingredients in a beaker under heat 70-75° C. until homogenous. Subsequently, the formulation can be cooled to standing room temperature (20-25° C.). Further, and if desired, additional ingredients can be added, for example, to modify the rheological properties of the composition or ingredients that provide benefits to skin.
*Excipients can be added, for example, to modify the rheological properties of the composition. Alternatively, the amount of water can be varied so long as the amount of water in the composition is at least 40% w/w, and preferably between 60 to 95% w/w.

Example 4

Additional Assays

Assays that can be used to determine the efficacy of any one of the ingredients or any combination of ingredients or compositions having said combination of ingredients disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

Production of Hyaluronic Acid:

Changes in the production of hyaluronic acid (HA) in human dermal fibroblasts due to each of the active ingredients, any one of the combination of ingredients, or compositions having said combinations disclosed in the specification can be measured. HA is a polysaccharide involved in stabilization of the structure of the matrix and is involved in providing turgor pressure to tissue and cells. As one non-limiting example, HA production in treated and non-treated adult human dermal fibroblasts (HDFa) cells can be determined using the Hyaluronan DuoSet ELISA kit from R&D Systems (DY3614). In this assay, for production of samples, subconfluent HDFa cells from Cascade Biologics (C-13-5C) are incubated at 37° C. and 10% CO2 in starvation medium (0.15% fetal bovine serum and 1% Penicillin Streptomycin solution in Dulbecco's Modified Eagle Medium) for 72 hours prior to treatment. The cells are then incubated with fresh starvation medium with either test compound, positive control (phorbol 12-myristate 13-acetate from Sigma-Aldrich (P1585) and platelet derived growth factor from Sigma-Aldrich (P3201)), or no additive for 24 hours. Media is then collected and frozen at −80° C. until use in the ELISA assay.

Briefly, the ELISA assay employs a quantitative sandwich enzyme immunoassay technique whereby a capture antibody specific for HA can be pre-coated onto a microplate. Standards and media from treated and untreated cells are pipetted into the microplate wells to enable any HA present to be bound by the immobilized antibody. After washing away any unbound substances, an enzyme-linked detection antibody specific for HA is added to the wells. Following a wash to remove any unbound antibody-enzyme reagent, a substrate solution is added to the wells to allow color development in proportion to the amount of HA bound in the initial step. The color development is stopped at a specific time and the intensity of the color at 450 nm can be measured using a microplate reader.

Elastin Stimulation Assay:

Elastin is a connective tissue protein that helps skin resume shape after stretching or contracting. Elastin is also an important load-bearing protein used in places where mechanical energy is required to be stored. Elastin is made by linking many soluble tropoelastin protein molecules, in a reaction catalyzed by lysyl oxidase. Elastin secretion and elastin fibers were monitored in cultured human fibroblasts by a direct ELISA sandwich method and analyzed using the Meso Scale Discovery system SECTOR 2400 Imaging system.

Laminin and Fibronectin Stimulation Assay:

Laminin and fibronectin are major proteins in the dermal-epidermal junction (DEJ) (also referred to as the basement membrane). The DEJ is located between the dermis and the epidermis interlocks forming fingerlike projections called rete ridges. The cells of the epidermis receive their nutrients from the blood vessels in the dermis. The rete ridges increase the surface area of the epidermis that is exposed to these blood vessels and the needed nutrients. The DEJ provides adhesion of the two tissue compartments and governs the structural integrity of the skin. Laminin and fibronectin are two structural glycoproteins located in the DEJ. Considered the glue that holds the cells together, laminin and fibronectin are secreted by dermal fibroblasts to help facilitate intra- and inter-cellular adhesion of the epidermal calls to the DEJ.

Laminin and fibronectin secretion were monitored by quantifying laminin and fibronectin in cell supernatants of cultured human fibroblasts treated for 3 days with culture medium with or without 1.0% final concentration of the test ingredient(s). Following incubation, laminin and fibronectin content was measured using immunofluorescent antibodies directed against each protein in an enzyme linked immunosorbant assay (ELISA).

Collagen Stimulation Assay:

Collagen is an extracellular matrix protein critical for skin structure. Increased synthesis of collagen helps improve skin firmness and elasticity. This bioassay was used to examine effects on the production of procollagen peptide (a precursor to collagen) by human epidermal fibroblasts. The endpoint of this assay was a spectrophotometric measurement that reflects the presence of procollagen peptide and cellular viability. The assay employed the quantitative sandwich enzyme immunoassay technique whereby a monoclonal antibody specific for procollagen peptide was pre-coated onto a microplate. Standards and samples were pipetted into the wells and any procollagen peptide present was bound by the immobilized antibody. After washing away any unbound substances, an enzyme-linked polyclonal antibody specific for procollagen peptide was added to the wells. Following a wash to remove any unbound antibody-enzyme reagent, a substrate solution was added to the wells and color was developed in proportion to the amount of procollagen peptide bound in the initial step. Color development was stopped and the intensity of the color at 450 nm was measured using a microplate reader.

For generation of samples and controls, subconfluent normal human adult epidermal fibroblasts (Cascade Biologics) were cultivated in standard DMEM growth medium with 10% fetal bovine serum (Mediatech) at 37° C. in 10% $CO_2$. The cells were treated with each of the tested ingredients and controls for 3 days. Following incubation, cell culture medium was collected and the amount of Type I procollagen peptide secretion was quantified using the sandwich enzyme linked immuno-sorbant assay (ELISA) from Takara (#MK101) as explained above.

Keratinocyte Monolayer Permeability:

Changes in the permeability of a keratinocyte monolayer due to each of the active ingredients, any one of the combination of ingredients, or compositions having said combinations disclosed in the specification can be measured. Keratinocyte monolayer permeability is a measure of skin barrier integrity. Keratinocyte monolayer permeability in treated and non-treated keratinocytes can be determined using, as a non-limiting example, the In Vitro Vascular Permeability assay by Millipore (ECM642). This assay analyzes endothelial cell adsorption, transport, and permeability. Briefly, adult human epidermal keratinocytes from Life Technologies (C-005-5C) can be seeded onto a porous collagen-coated membrane within a collection well. The keratinocytes are then incubated for 24 hours at 37° C. and 5% $CO2$ in Epilife growth media with calcium from Life Technologies (M-EP-500-CA) supplemented with Keratinocyte Growth Supplement (HKGS) from Life Technologies (S-101-5). This incubation time allows the cells to form a monolayer and occlude the membrane pores. The media is then replaced with fresh media with (test sample) or without (non-treated control) test compounds/extracts and the keratinocytes are incubated for an additional 48 hours at 37° C. and 5% $CO_2$. To determine permeability of the keratinocyte monolayer after incubation with/without the test compound/extract, the media is replaced with fresh media containing a high molecular weight Fluorescein isothiocyanate (FITC)-Dextran and the keratinocytes are incubated for 4 hours at 37° C. and 5% $CO2$. During the 4 hours incubation, FITC can pass through the keratinocytes monolayer and porous membrane into the collection well at a rate proportional to the monolayer's permeability. After the 4 hour incubation, cell viability and the content of FITC in the collection wells can be determined. For the FITC content, the media in the collection well is collected and fluorescence of the media determined at 480 nm (Em) when excited at 520 nm. Percent permeability and percent change in comparison to the non-treated controls can be determined by the following equations: Percent Permeability=((Mean Ex/Em of test sample)/Mean Ex/Em untreated control)*100; Percent Change=Percent Permeability of test sample−Percent Permeability of untreated control.

Antioxidant (AO) Assay:

An in vitro bioassay that measures the total anti-oxidant capacity of any one of the ingredients, combination of ingredients, or compositions having said combinations disclosed in the specification. The assay relies on the ability of antioxidants in the sample to inhibit the oxidation of ABTS® (2,2'-azino-di-[3-ethylbenzthiazoline sulphonate]) to ABTS®.+ by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS oxidation is compared with that of Trolox, a water-soluble tocopherol analogue, and is quantified as molar Trolox equivalents. Anti-Oxidant capacity kit #709001 from Cayman Chemical (Ann Arbor, Michigan USA) can be used as an in vitro bioassay to measure the total anti-oxidant capacity of each of any one of the active ingredients, combination of ingredients, or compositions having said combinations disclosed in the specification. The protocol can be followed according to manufacturer recommendations.

B16 Pigmentation Assay:

Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilizes B16-F1 melanocytes (ATCC), an immortalized mouse melanoma cell line, to analyze the effect of compounds on melanogenesis. The endpoint of this assay is a spectrophotometric measurement of melanin production and cellular viability. B16-F1 melanocytes, can be cultivated in standard DMEM growth medium with 10% fetal bovine serum (Mediatech) at 37° C. in 10% $CO2$ and then treated with any one of the active ingredients, combination of ingredients, or compositions having said combinations disclosed in the specification for 6 days. Following incubation, melanin secretion is measured by absorbance at 405 nm and cellular viability is quantified.

Mushroom Tyrosinase Activity Assay:

In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (Sigma) can be incubated with its substrate L-Dopa (Fisher) in the presence or absence of each of the active ingredients, any one of the combination of ingredients, or compositions having said combinations disclosed in the specification. Pigment formation can be evaluated by colorimetric plate reading at 490 nm. The percent inhibition of mushroom tyrosinase activity can be calculated compared to non-treated controls to determine the ability of test ingredients or combinations thereof to inhibit the activity of purified enzyme. Test extract inhibition was compared with that of kojic acid (Sigma).

Matrix Metalloproteinase 3 and 9 Enzyme Activity (MMP3; MMP9) Assay:

An in vitro matrix metalloprotease (MMP) inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2-mercapto-4-methylpentanoyl]-LG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm (E=13,600 M-lcm-1 at pH 6.0 and above 7). The active ingredients, any one of the combination of ingredients, or compositions having said combinations disclosed in the specification can be assayed.

Matrix Metalloproteinase 1 Enzyme Activity (MMP1) Assay:

An in vitro matrix metalloprotease (MMP) inhibition assay. MMPs are extracellular proteases that play a role in many normal and disease states by virtue of their broad substrate specificity. MMP1 substrates include collagen IV. The Molecular Probes Enz/Chek Gelatinase/Collagenase Assay kit (#E12055) utilizes a fluorogenic gelatin substrate to detect MMP1 protease activity. Upon proteolytic cleavage, bright green fluorescence is revealed and may be monitored using a fluorescent microplate reader to measure enzymatic activity.

The Enz/Chek Gelatinase/Collagenase Assay kit (#E12055) from Invitrogen is designed as an in vitro assay to measure MMP1 enzymatic activity. The active ingredients, any one of the combination of ingredients, or compositions having said combinations disclosed in the specification can be assayed. The assay relies upon the ability of purified MMP1 enzyme to degrade a fluorogenic gelatin substrate. Once the substrate is specifically cleaved by MMP1 bright green fluorescence is revealed and may be monitored using a fluorescent microplate reader. Test materials are incubated in the presence or absence of the purified enzyme and substrate to determine their protease inhibitor capacity.

Cyclooxygenase (COX) Assay:

An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. The Colormetric COX (ovine) Inhibitor screening assay (#760111, Cayman Chemical) can be used to analyze the effects of each of the active ingredients, any one of the combination of ingredients, or compositions having said combinations disclosed in the specification on the activity of purified cyclooxygnase enzyme (COX-1 or COX-2). According to manufacturer instructions, purified enzyme, heme and test extracts can be mixed in assay buffer and incubated with shaking for 15 min at room temperature. Following incubation, arachidonic acid and colorimetric substrate can be added to initiate the reaction. Color progression can be evaluated by colorimetric plate reading at 590 nm. The percent inhibition of COX-1 or COX-2 activity can be calculated compared to non-treated controls to determine the ability of test extracts to inhibit the activity of purified enzyme.

Lipoxygenase (LO) Assay:

An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotrienes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid. The Colorimetric LO Inhibitor screening kit (#760700, Cayman Chemical) can be used to determine the ability of each of the active ingredients, any one of the combination of ingredients, or compositions having said combinations disclosed in the specification to inhibit enzyme activity. Purified 15-lipoxygenase and test ingredients can be mixed in assay buffer and incubated with shaking for 10 min at room temperature. Following incubation, arachidonic acid can be added to initiate the reaction and the mixtures can be incubated for an additional 10 min at room temperature. Colorimetric substrate can be added to terminate catalysis and color progression can be evaluated by fluorescence plate reading at 490 nm. The percent inhibition of lipoxyganse activity can be calculated compared to non-treated controls to determine the ability of each of the active ingredients, any one of the combination of ingredients, or compositions having said combinations disclosed in the specification to inhibit the activity of purified enzyme.

Elastase Assay:

ENZCHEK® Elastase Assay (Kit #E-12056) from Molecular Probes (Eugene, Oregon USA) can be used as an in vitro enzyme inhibition assay for measuring inhibition of elastase activity for each of the active ingredients, any one of the combination of ingredients, or compositions having said combinations disclosed in the specification. The EnzChek kit contains soluble bovine neck ligament elastin that can be labeled with dye such that the conjugate's fluorescence can be quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide, N-methoxysuccinyl-Ala-Ala-Pro-Val-chloromethyl ketone, can be used as a selective, collective inhibitor of elastase when utilizing the EnzChek Elastase Assay Kit for screening for elastase inhibitors.

Oil Control Assay:

An assay to measure reduction of sebum secretion from sebaceous glands and/or reduction of sebum production from sebaceous glands can be assayed by using standard techniques known to those having ordinary skill in the art. In one instance, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion).

Erythema Assay:

An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with the active ingredients, any one of the combination of ingredients, or compositions having said combinations disclosed in the specification. Repeat measurements can be taken at regular intervals to determine the formula's ability to reduce redness and irritation.

Skin Clarity and Reduction in Freckles and Age Spots Assay:

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether each of the active ingredients, any one of the combination of ingredients, or compositions having said combinations disclosed in the specification is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay:

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay:

Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay:

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay with Methods Disclosed in Packman et al. (1978):

Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Appearance of Lines and Wrinkles Assay with Replicas:

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and are of the replicas covered by wrinkles or fine lines was determined.

Skin Firmness Assay with a Hargens Ballistometer:

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer:

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Surface Contour of the Skin Assay with a Profilometer/Stylus Method:

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay:

In other non-limiting aspects, the efficacy of each of the active ingredients, any one of the combination of ingredients, or compositions having said combinations disclosed in the specification can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing each of the active ingredients, any one of the combination of ingredients, or compositions having said combinations disclosed in the specification or with the base alone as a control. Alternatively, an untreated sample of the skin analog can be used as a control.

Inhibition of Hyaluronidase Activity:

Changes in the activity of hyaluronidase due to each of the active ingredients, any one of the combination of ingredients, or compositions having said combinations disclosed in the specification can be measured. Hyaluronidase is an enzyme that degrades HA. HA is a polysaccharide involved in stabilization of the structure of the matrix and is involved in providing turgor pressure to tissue and cells. As one non-limiting example, hyaluronidase activity can be determined using an in vitro protocol modified from Sigma-Aldrich protocol #EC 3.2.1.35. Briefly, hyaluronidase type 1-S from Sigma-Aldrich (H3506) is added to microplate reaction wells containing test compound or controls. Tannic acid can be used as a positive control inhibitor, no test compound can be added for the control enzyme, and wells with test compound or positive control but without hyaluronidase can be used as a background negative control. The wells are incubated at 37° C. for 10 minutes before addition of substrate (HA). Substrate is added and the reactions incubated at 37° C. for 45 minutes. A portion of each reaction solution is then transferred to and gently mixed in a solution of sodium acetate and acetic acid pH 3.75 to stop that portion of the reaction (stopped wells). The stopped wells and the reaction wells should both contain the same volume of solution after addition of the portion of the reaction solution to the stopped wells. Both the reaction wells and the stopped wells are incubated for 10 minutes at room temperature. Absorbance at 600 nm is then measured for both the reaction wells and the stopped wells. Inhibition can be calculated using the following formulas: Inhibitor (or control) activity=(Inhibitor stopped wells absorbance at 600 nm−inhibitor reaction wells absorbance at 600 nm); Initial activity=control enzyme absorbance at 600 nm; Percent Inhibition=[(Initial activity/Inhibitor Activity)*100]−100.

Peroxisome Proliferator-Activated Receptor Gamma (PPAR-γ) Activity:

Changes in the activity of PPAR-γ due to each of the active ingredients, any one of the combination of ingredients, or compositions having said combinations disclosed in the specification can be measured. PPAR-γ is a receptor critical for the production of sebum. As one non-limiting example, the activity of PPAR-γ can be determined using a bioassay that analyzes the ability of a test compound or composition to inhibit binding of a ligand. Briefly, fluorescent small-molecule pan-PPAR ligand, FLUORMONE™ Pan-PPAR Green, available from Life Technologies (PV4894), can be used to determine if test compounds or compositions are able to inhibit binding of the ligand to PPAR-γ. The samples wells include PPAR-γ and fluorescent ligand and either: test compound or composition (test); a reference inhibitor, rosiglitazone (positive control); or no test compound (negative control). The wells are incubated for a set period of time to allow the ligand opportunity to bind the PPAR-γ. The fluorescence polarization of each sample well can then be measured and compared to the negative control well to determine the percentage of inhibition by the test compound or composition.

Cytokine Array:

Human epidermal keratinocytes are cultured to 70-80% confluency. The media in the plate is aspirated and 0.025% trypsin/EDTA is added. When the cells became rounded, the culture dish is gently tapped to release the cells. The trypsin/EDTA containing cells are removed from the culture dish and neutralized. Cells are centrifuged for 5 min. at 180×g to form a pellet of cells. The supernatant is aspirated. The resulting pellet is resuspended in EPILIFE™ media (Cascade Biologics). The cells are seeded in 6-well plates at approximately 10-20% confluency. After the cells became approximately 80% confluent, the media is aspirated and 1.0 ml of EPILIFE™, along with phorbol 13-Myristate 12-acetate ("PMA") (a known inducer of inflammation) and the test composition dilutions are added to two replicate wells (i.e., 1.0% (100 μl of 100× stock) and 0.1% (10 μl of 100× stock) test compositions are diluted into a final volume of 1 ml EpiLife Growth Medium). The media is gently swirled to ensure adequate mixing. In addition, 1.0 ml of EPILIFE™ is added to the control wells, with and without additional PMA. The plates are then incubated at 37±1° C. and 5.0±1% $CO_2$ for approximately 5 hours after dosing. Following this 5-hour incubation, all media is collected in conical tubes and frozen at −70° C.

For analysis, a 16-pad hybridization chamber is attached to 16-pad FAST slides arrayed in triplicate with 16 anti-cytokine antibodies plus experimental controls (Whatman BioSciences), and the slides are placed into a FASTFrame (4 slides per frame) for processing. Arrays are blocked for 15 min. at room temperature using 70 ml S&S Protein Array Blocking buffer (Whatman Schleicher and Scheull). Blocking buffer is removed and 70 ml of each supernatant sample is added to each array. Arrays are incubated for 3 hours at room temperature with gentle agitation. Arrays are washed 3 times with TBS-T. Arrays are treated with 70 ml of an antibody cocktail, containing one biotinylated antibody corresponding to each of the arrayed capture antibodies. Arrays are incubated for 1 hour at room temperature with gentle agitation. Arrays are washed 3 times with TBS-T. Arrays are incubated with 70 ml of a solution containing streptavidin-Cy5 conjugate for 1 hour at room temperature with gentle agitation. Arrays are washed 3 times with TBS-T, quickly rinsed in de-ionized water, and dried.

Slides can be imaged in a Perkin-Elmer ScanArray 4000 confocal fluorescent imaging system. Array images can be saved and analyzed using Imaging Research ArrayVision software. Briefly, spot intensities are determined by subtracting background signal. Spot replicates from each sample condition can be averaged and then compared to the appropriate controls.

Endothelial Tube Formation:

Endothelial tube formation is involved in angiogenesis and micro-vessel capillary formation. Capillary formation and angiogenesis may contribute to redness and rosacea of the skin. The ability for endothelial cells to form tubes in the presence or absence of test extracts and compounds may be determined using a capillary tubule disruption assay with pre-formed primary human umbilical vein endothelial cells (HUVEC) in a cell culture system.

Briefly, HUVECs are cultured in vitro on Extracellular Matrix, which stimulates the attachment and tubular morphogenesis of endothelial cells to form capillary-like lumen structures. These in vitro formed capillary tubules are similar to human blood vessel capillaries in many aspects. The capillary tube assay is based on this phenomenon and is used for evaluation of potential vasculature targeting agents.

HUVEC cultures are grown in a 5% $CO_2$ 37° C. cell incubator. The full growth medium for HUVECs is Endothelial Cell Basal Medium (EBM) supplemented with 2% fetal bovine serum (FBS), 12 µg/ml bovine brain extract, 1 µg/ml hydrocortisone, and 1 µg/ml GA-1000 (gentamicin-amphothericin). HUVEC cultures between passage 3 and 8 may be used for all assay experiments.

HUVECs are pre-labeled with fluorescent agent Calcein AM and seeded in Extracellular Matrix coated 96-well culture plate with their full growth medium. After about four hours of the morphogenesis process, the endothelial capillary tubes should be formed. Then, test agent in designed doses in 50 µl volume is applied into the formed capillary tubule cultures as treatment conditions. The no-treatment controls can be added with vehicle of test agents. SUTENT®, a FDA approved anti-angiogenic drug one concentration can be included as assay performance control. After about six hours of treatment, the endothelial tubule morphology in each well is examined by microscopy, imaged, and the capillary disrupting activities under treatment conditions can be quantitatively analyzed. Each test conditions can be conducted in duplicate wells, including controls.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Cosmetic Ingredient Dictionary, Third Edition, CTFA, 1982
International Cosmetic Ingredient Dictionary, Fourth edition, CTFA, 1991
International Cosmetic Ingredient Dictionary and Handbook, Tenth Edition, CTFA, 2004
International Cosmetic Ingredient Dictionary and Handbook, Twelfth Edition, CTFA, 2008
Sodium Hyaluronate Powder Product Data Sheet, Tri-K Industries, Inc., 2008
HyaClear® Solution Presentation, Tri-K Industries, Inc., 2016

The invention claimed is:

1. A method of moisturizing skin and one or more of reducing inflammation of skin or increasing antioxidant capacity of skin, the method comprising topically applying to dry, inflamed, and/or oxidized skin a topical composition comprising an effective amount of a combination of:
   (a) saccharide isomerate;
   (b) sodium carrageenan;
   (c) sea salt from the Baltic Sea; and
   (d) sodium hyaluronate,
wherein the skin is moisturized, and one or more of inflammation in the skin is reduced and/or oxidants in the skin are reduced, and wherein the amount of sodium carrageenan and sea salt is effective to promote production of hyaluronic acid and production of ceramides.

2. The method of claim 1, wherein the composition comprises 0.001 to 5% w/w of saccharide isomerate, 0.001 to 5% w/w of sodium carrageenan, 0.0001 to 5% w/w of sea salt, and 0.0001 to 1% w/w of sodium hyaluronate.

3. The method of claim 1, wherein:
   the amount of saccharide isomerate is effective to condition and moisturize the skin, decrease TNF-α production, increase skin conductance, and/or increase antioxidant capacity; and/or
   the amount of sodium carrageenan and sea salt is effective to promote hydration of the skin and strengthen and repair skin, increase epidermal and dermal production of hyaluronic acid, and/or increase stratum corneum and epidermal production of ceramides.

4. The method of claim 1, wherein the composition comprises water.

5. The method of claim 4, wherein the composition comprises 75 to 95% w/w of water.

6. The method of claim 1, wherein the composition comprises glycerin, disodium EDTA, benzophenone-4, butylene glycol, and triethanolamine.

7. The method of claim 6, wherein the composition comprises 0.5 to 8% w/w of glycerin, 0.005 to 1% w/w of disodium EDTA, 0.005 to 1% w/w of benzophenone-4, 1 to 10% w/w of butylene glycol, and 0.01 to 1% w/w of triethanolamine.

8. The method of claim 1, wherein the composition comprises 0.1 to 3% w/w of bis-PEG-18 methyl ether dimethyl silane and 0.01 to 1% w/w of xanthan gum.

9. The method of claim 1, wherein the composition comprises 0.1 to 5% w/w of c-isostearyl alcohol.

10. The method of claim 1, wherein the composition comprises 1 to 10% w/w of diisostearyl malate.

11. The method of claim 1, wherein the topical composition is topically applied to dry skin.

12. The method of claim 1, wherein the topical composition is topically applied to inflamed skin.

13. The method of claim 1, wherein the topical composition is topically applied to oxidized skin.

\* \* \* \* \*